United States Patent [19]

Margaria

[11] Patent Number: 5,605,583
[45] Date of Patent: Feb. 25, 1997

[54] METALLURGICAL SILICON WITH CONTROLLED MICROSTRUCTURE FOR THE PREPARATION OF HALOGENOSILANES

[75] Inventor: Thomas Margaria, Chedde, France

[73] Assignee: Pechiney Electrormetallurgie, Courbevoie, France

[21] Appl. No.: 390,022

[22] Filed: Feb. 17, 1995

[30] Foreign Application Priority Data

Feb. 25, 1994 [FR] France ................... 94 02487

[51] Int. Cl.$^6$ ................................. C01B 33/02
[52] U.S. Cl. .................... 148/405; 420/578; 423/348
[58] Field of Search ................. 148/405; 420/578; 423/348

[56] References Cited

U.S. PATENT DOCUMENTS

| | | | |
|---|---|---|---|
| 4,605,055 | 8/1986 | Allen, Jr. | 164/479 |
| 4,687,606 | 8/1987 | Crosbie | 420/578 |
| 4,895,969 | 1/1990 | Feldner et al. | 556/472 |
| 5,094,832 | 3/1992 | Forwald et al. | 423/348 |
| 5,128,116 | 7/1992 | Forwald et al. | 423/348 |

FOREIGN PATENT DOCUMENTS

| | | | |
|---|---|---|---|
| 201199 | 11/1986 | European Pat. Off. | 423/348 |
| 402665 | 12/1990 | European Pat. Off. | |
| 494837 | 7/1992 | European Pat. Off. | 423/348 |
| 522844 | 1/1993 | European Pat. Off. | |
| 4037021 | 5/1991 | Germany . | |
| 59-78920 | 5/1984 | Japan | 423/348 |

*Primary Examiner*—George Wyszomierski
*Attorney, Agent, or Firm*—Dennison, Meserole, Pollack & Scheiner

[57] ABSTRACT

A metallurgical silicon with controlled microstructure for the preparation of halogenosilanes, characterized by an image of the microstructure obtained with the scanning electron microscope which is processed by binarization between an intermetallic phase and a silicon matrix, with expansion in zones corresponding to the intermetallic phase with an extension of about 10 μm around these zones. The ratio of the surface fraction of the intermetallic phase after expansion to the intermetallic phase before expansion, $S/S_0$, is between 20 and 40. The silicon according to the invention assures an elevated reactivity in the Rochow reaction for the production of halogenosilanes intended for the preparation of silicones.

3 Claims, 2 Drawing Sheets

METALLURGICAL SILICON WITH CONTROLLED MICROSTRUCTURE FOR THE PREPARATION OF HALOGENOSILANES

FIELD OF THE INVENTION

The invention relates to a particular quality of metallurgical silicon with a controlled microstructure, in particular at the level of the distribution of the intermetallic compounds due to minor elements present in the silicon. This quality is especially well suited to the reaction for synthesis of alkyl or aryl halogenosilanes.

DESCRIPTION OF RELATED ART

The synthesis of alkyl or aryl halogenosilanes by reaction, between 250° and 350° C., of a halogenated hydrocarbon on with silicon in the presence of a copper-based catalyst is known from U.S. Pat. No. 2,380,995, issued on Aug. 7, 1945 to Rochow.

This reaction, known as the Rochow reaction, has attained major industrial development, and in particular is the basis for the entire silicon industry. It is done in general with methyl chloride, $CH_3Cl$, and leads to a mixture of different methylchlorosilanes, such as monomethyltrichlorosilane and dimethyldichlorosilane. Since this latter product is the most highly sought, the reaction is carried out in such a way that the proportion of that product is maximized in the mixture of silanes obtained, and this proportion is called the selectivity of the reaction. Moreover, it is important to produce the maximum quantity of silanes per unit of time, and the value of this gravimetric flow is called reactivity. Since the initial patent to Rochow, numerous research projects have been dedicated to improving these two parameters by varying the technology of the process, the catalysts, and the chemical composition of the silicon, the silicon being an industrial product containing a certain number of minor elements.

For economic reasons, the silicon used in the Rochow reaction is in fact metallurgical silicon, produced by carboreduction of silica in an electric oven, and then refined to regulate the amount of its principal minor elements and solidified, either in the form of ingots or in the form of granules. These products are then reduced to powder by grinding.

This metallurgical silicon contains a certain number of principal minor elements, essentially calcium, aluminum and iron, each of which is present in amounts of between 0.01 and 1% by weight, amounts which are adjusted in the course of the refining process in order to meet the specifications required by the market. The silicon also contains secondary minor elements entrained by the primary materials, in a total quantity that is generally between 10 and 500 ppm, which are metalloids (P, B, S, C) or metals (Ti, Ca, Mg, Mn, Ni, V, Zr).

These minor elements occur in the form of intermetallic compounds, and those formed by the principal elements may be binary ($FeSi_2$, $CaSi_2$), ternary ($Fe_5Al_8Si_7$, $CaAl_2Si_2$, $FeSi_2Al_3$) or quaternary ($Fe_4Al_6CaSi_8$). These various intermetallic compounds are described in a publication by the present applicants, T. Margaria, J. C. Anglezio, C. Servant, "Intermetallic Compounds in Metallurgical Silicon", INFACON 6, Proceedings of the 6th International Ferroalloys Congress, Capetown, Vol. 1, SAIMM Johannesburg, 1992, pp. 209–214. This publication illustrates the conditions of formation of intermetallic compounds, particularly as a function of the speed of solidification of the silicon, and the influence of certain compounds on the selectivity and reactivity of the Rochow reaction. Other work has also demonstrated the role of the chemical composition of intermetallic compounds. For instance, German Patent Application DE 4,037,021 of the ELKEM corporation claims a silicon intended for the Rochow reaction, in which the impurities are in the form of $FeAl_3Si_2$ and $Fe_4Si_6Al_4Ca$ compounds- In addition, it has been proposed that the reactivity in the Rochow reaction be improved by varying the granulometry and the mode by which the silicon powder is obtained. Thus, European Patents EP 350,683 of Bayer and EP 372,918 of ELKEM contend that the use of atomized silicon enables a substantial increase in reactivity. However, atomization is not used industrially for producing the silicon intended for silane synthesis,

SUMMARY OF THE INVENTION

The object of the invention is to provide a metallurgical silicon that leads to elevated reactivity in the Rochow reaction by controlling the microstructure of the silicon produced.

To achieve this and other objects, the invention is directed to a metallurgical silicon with controlled microstructure for the preparation of halogenosilanes, characterized in that when an image of the microstructure obtained with the scanning electron microscope is processed by binarization between an intermetallic phase and a silicon matrix, with subsequent expansion of the zones corresponding to the intermetallic phase with an extension of 10 µm around these zones the ratio $S/S_0$ of the surface fractions of the intermetallic phase between the expanded image and the image before expansion is between 20 and 40.

The invention also relates to a method of characterizing metallurgical silicon for the preparation of halogenosilanes, comprising:

making an image of the silicon microstructure with a scanning electron microscope in the back scattering electron mode, and contrasting the mean atomic number;

treating the image obtained with image analysis software with smoothing of the grey levels, binarization between a silicon matrix and an intermetallic phase, and expansion of the zones corresponding to the intermetallic phase; and comparing the surface fractions of the intermetallic phases before and after a defined expansion around zones corresponding to the intermetallic phase, Applicants have unexpectedly discovered that the technique of expansion used in image analysis makes it possible to predict, over a certain range, the behavior of the silicon in the Rochow reaction, and more particularly its reactivity.

While not wishing to be held to any particular theory, in an attempt to explain this relationship, Applicants hypothesize that the more highly dispersed the intermetallic compounds are, the more they constitute attack sites for the reaction, and the more the reaction has a tendency to propagate rapidly within the entire mass of the silicon. The more highly dispersed the intermetallic compounds are, the greater their surface fraction after expansion in image analysis will be. However, it appears that beyond a certain level, the increase in dispersion goes counter to the reactivity, and there is accordingly an optimal range of dispersion that promotes the reactivity.

DETAILED DESCRIPTION OF THE INVENTION

The method of characterization according to the invention comprises first preparing specimens of the metallurgical silicon having a microstructure to be controlled. This preparation includes coating with a colorless copper-based conductive resin, prepolishing the silicon with carbon paper, impregnation in a vacuum, and finally, polishing with diamond-impregnated felt. The specimens are analyzed in the scanning electron microscope using the buck scattering electron mode (BSE) and contrasting the mean atomic number. The regions of intermetallic compounds appear white relative to the silicon matrix. By adjusting the brilliance, a well-defined and reproducible mean grey level is achieved, in such a way as to remain always within the same conditions.

Work can be done at relatively low enlargements (for example 200×), which allows a large analysis field (500×500 µm).

The image obtained with the scanning electron microscope is then processed with image analyzing software. The first step consists of smoothing the image into grey levels to eliminate imperfections due to the information sampling. The next step is binarization of the image, which makes its possible to separate the silicon and intermetallic phases. In order to properly take into account the very fine phases, a resolution of 1024×1024 dots per image is used. Next, the crude surface fraction occupied by the intermetallic phases in the analysis field in question is measured. This measurement is done for a number of fields such that the cumulative surface fraction tends to stabilize around a mean value.

Figure 1:
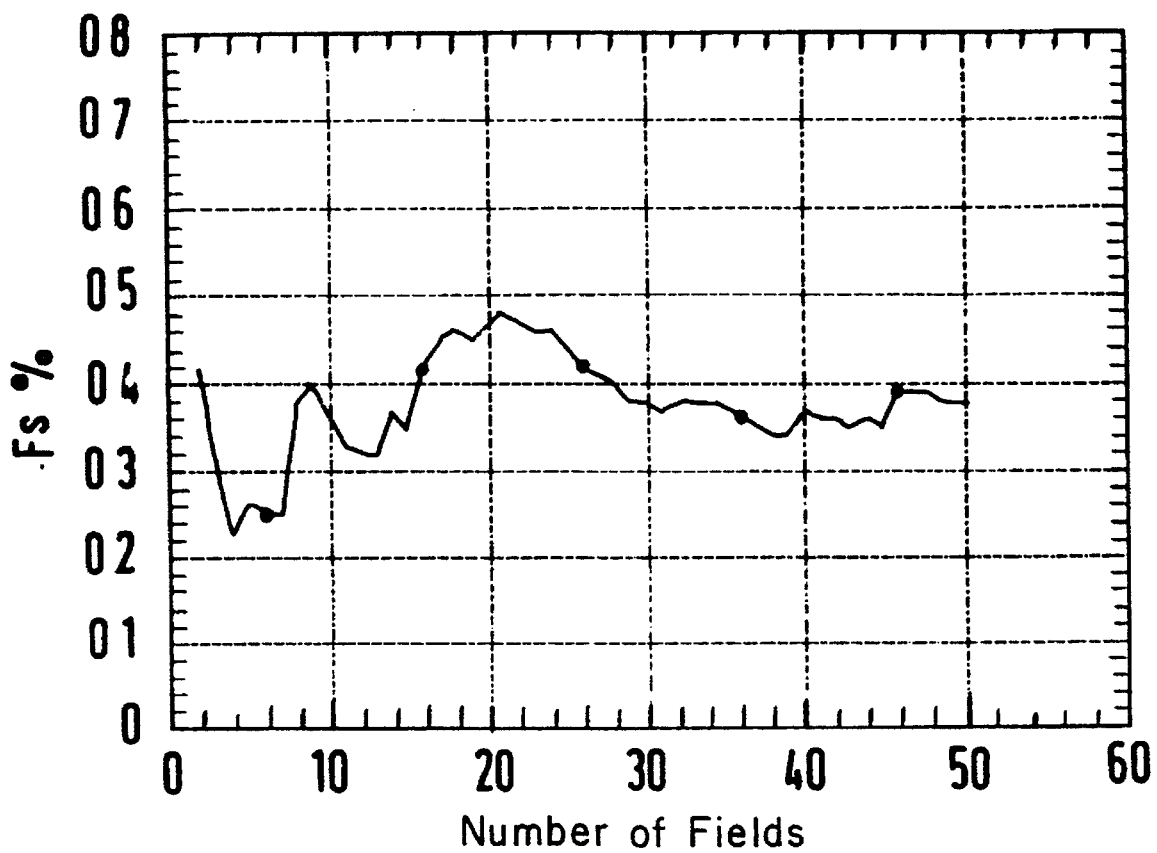
FIG. 1 is a graph of surface fraction in percent vs. number of fields for a range up to 50 fields.

FIG. 1 is a graph showing an example where the cumulative surface fraction tends to stabilize beyond 30 fields. In such a case, measurements will be done with 50 fields.

The next step is the expansion of the zones corresponding to the intermetallic compounds, by successive increments of from 1 to 10, each corresponding to an extension of 1.8 µm on the outside of these zones, and the surface fraction of the intermetallic phase is measured upon each increment of expansion.

Figure 2A:
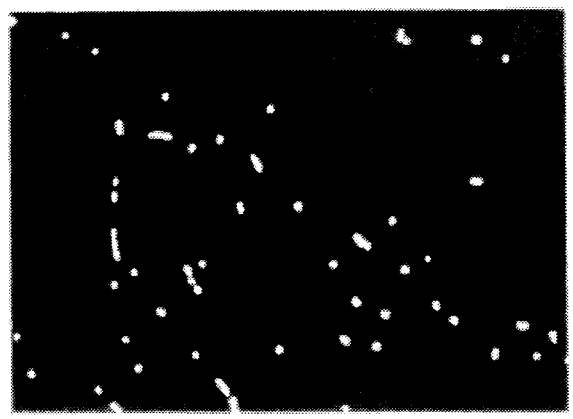
FIGS. 2 and 2b are photographic representations of binary images before and after expansion, respectively, for a silicon sample.
Figure 2B:
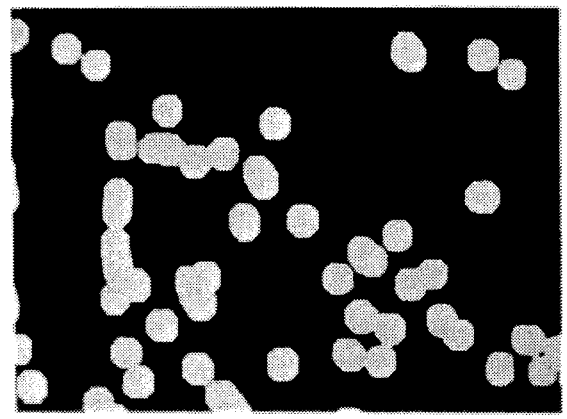

FIGS. 2 and 2b respectively show the binary images before and after an expansion with an increment of 9, for a silicon specimen in which the intermetallic compounds are not highly dispersed and conversely are clumped into quite large regions.

Figure 3A:
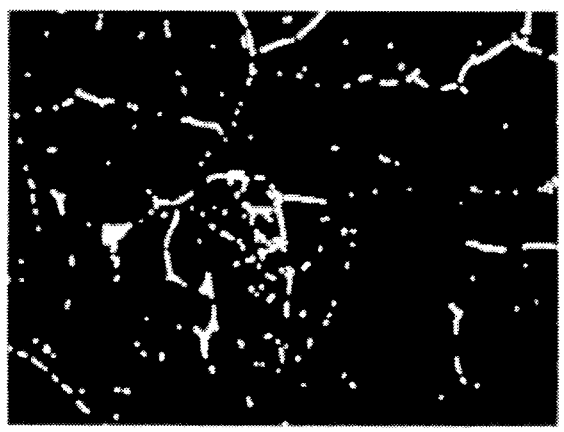
FIGS. 3 and 3b are photographic representations of binary images before and after expansion, respectively, for another silicon sample.
Figure 3B:
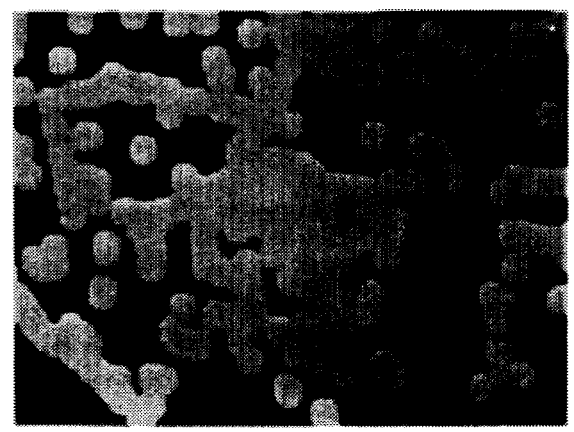

FIGS. 3 and 3b, under the same conditions, show the binary images corresponding to a specimen of silicon according to the invention, with the intermetallic phases well dispersed.

It can be seen that beginning at a practically identical crude surface fraction in both cases, the white surface fraction, corresponding to the intermetallic phases, is very greatly superior in the second case, with an elevated rate of expansion.

To obtain a microstructure according to the invention it is necessary for the solidification of the silicon to take place at a sufficient chilling rate, preferably between 400° and 600° C./s, even though this is not the only parameter that affects the dispersion of the intermetallic compounds. It has been confirmed that among the various possible solidification techniques, granulation assisted with a water jet most often makes it possible to obtain the microstructure sought. In this technique, as with classical granulation, one uses a granulation head placed above a dish containing a volume of water whose surface is located between 30 and 60 cm below the head.

The liquid metal poured onto the granulation head disperses into a nearly continuous liquid sheet, which naturally disperses into droplets before reaching the surface of the water of the dish. By projecting a shower of water under pressure onto the secondary sheet of liquid silicon coming from the granulation head, one obtains faster dispersion and finer droplets, which then chill more quickly.

This apparatus makes it possible to attain a chilling rate of approximately 500° C./s, which is favorable to obtaining the desired microstructure according to the invention. In addition, the explosions that threaten to occur in a conventional granulation installation, even one especially dimensioned for processing silicon, are thus averted.

Conversely, solidification in the form of ingots, either individually poured ingots of a thickness between 10 and 20 cm or ingots poured in a succession of ingot molds and 4 to 5 cm in thickness, optionally with chilling of the succession accelerated by spraying wager, does not make it possible to obtain the microstructure sought throughout the entire product.

Moreover, the microstructure produced by solidification by atomization, although corresponding to an elevated chilling rate and leading, in the characterization test according to the invention: to an elevated ratio of the surface fractions after and before expansion of the intermetallic phase, surprisingly results in a lessening of the reactivity.

This shows that the characterization method of the invention makes it possible to determine an optimal microstructure range that allows an elevated level of reactivity for the synthesis of chlorosilanes.

EXAMPLE

Metallurgical silicon having a chemical composition adapted to the specifications of silicone producers and containing, by weight, 0.25% iron, 0.1% aluminum and 0.04% calcium as principle minor elements was produced.

A portion of this silicon in the liquid state was poured into ingots 10 cm thick in a conventional ingot molding installation, and another portion was poured into a line of ingot molds chilled in air producing ingots 5 cm thick. Another portion was poured in the same of ingot molds, with chilling by spraying with water. A further portion was granulated in water, with the resulting silicon beads not exceeding 10 mm in diameter, with another portion being granulated by the process of granulation assisted with a water jet as described above. Finally, a portion was atomized into particles whose size was between 50 and 250 µm.

Specimens of products prepared by the six methods described were subjected to the characterization method according to the invention, with image processing by expansion done for 30 analysis fields. For the six specimens, the mean surface fraction of the intermetallic phase before expansion and the mean surface fraction of this same phase after six expansion increments of 1.8 µm each, hence an expansion of 10.8 µm, were measured.

The ratios of surface fractions obtained, $S/S_0$, are as follows:

Ingots poured individually: 3
Ingots poured in a non-chilled line: 8
Ingots poured in a chilled line: 12
Conventional granulation with water: 17
Granulation assisted by water jet: 31
Atomization: 48

Chloromethylation tests demonstrate that the silicon granulated by the water jet-assisted granulation method has a reactivity greater by at least 10% than that of the silicon solidified by any other method.

What is claimed is:

1. Metallurgical silicon for the preparation of halogenosilanes, comprising a microstructure characterized by an image obtained with a scanning electron microscope processed by binarization in zones between an intermetallic phase and a silicon matrix, and expanded with an extension of about 10 μm around the zones with determination of surface fraction of the intermetallic phase before and after expansion, the surface fraction of the intermetallic phase after expansion and the surface fraction of the intermetallic phase before expansion being in a ratio $S/S_0$ of between 20 and 40.

2. Metallurgical silicon according to claim 1, including Ca, Fe and Al, each present in an amount of between 0.01 and 1% by weight.

3. Metallurgical silicon for the preparation of halogenosilanes, produced by chilling droplets of liquid silicon smaller than 10 mm in size at a rate of 400° to 600° C./sec, and comprising a controlled microstructure characterized by an image obtained with a scanning electron microscope processed by binarization in zones between an intermetallic phase and a silicon matrix, and expanded with an extension of about 10 μm around the zones with determination of surface fraction of the intermetallic phase before and after expansion, the surface fraction of the intermetallic phase after expansion and the surface fraction before expansion being in a ratio $S/S_0$ of between 20 and 40.

* * * * *

UNITED STATES PATENT AND TRADEMARK OFFICE
CERTIFICATE OF CORRECTION

PATENT NO. : 5,605,583
DATED : February 25, 1997
INVENTOR(S) : THOMAS MARGARIA

It is certified that error appears in the above-indentified patent and that said Letters Patent is hereby corrected as shown below:

Title page:

after [73] Assignee: change "Pechiney Electrormetallurgie" to --Pechiney Electrometallurgie--.

Signed and Sealed this

Twentieth Day of May, 1997

Attest:

BRUCE LEHMAN

Attesting Officer

Commissioner of Patents and Trademarks